United States Patent
Pappas et al.

(10) Patent No.: US 9,539,188 B2
(45) Date of Patent: Jan. 10, 2017

(54) ANTIPERSPIRANT ACTIVE COMPOSITIONS AND MANUFACTURE THEREOF

(71) Applicant: Colgate-Palmolive Company, New York, NY (US)

(72) Inventors: Iraklis Pappas, Pennsauken, NJ (US); Long Pan, Cherry Hill, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/807,946

(22) Filed: Jul. 24, 2015

(65) Prior Publication Data

US 2015/0328097 A1   Nov. 19, 2015

Related U.S. Application Data

(62) Division of application No. 13/882,488, filed as application No. PCT/US2010/055030 on Nov. 2, 2010, now abandoned.

(51) Int. Cl.
| A61K 8/28 | (2006.01) |
|---|---|
| A61K 8/44 | (2006.01) |
| A61K 8/26 | (2006.01) |
| A61Q 15/00 | (2006.01) |

(52) U.S. Cl.
CPC . *A61K 8/28* (2013.01); *A61K 8/26* (2013.01); *A61K 8/44* (2013.01); *A61Q 15/00* (2013.01); *A61K 2800/80* (2013.01)

(58) Field of Classification Search
None
See application file for complete search history.

(56) References Cited

U.S. PATENT DOCUMENTS

| 3,979,510 A | 9/1976 | Rubino |
| 3,991,176 A | 11/1976 | Rubino |
| 4,359,456 A | 11/1982 | Gosling et al. |
| 4,871,525 A | 10/1989 | Giovanniello et al. |
| 4,900,534 A | 2/1990 | Inward |
| 5,330,751 A | 7/1994 | Curtin et al. |
| 5,348,720 A | 9/1994 | Vincenti et al. |
| 5,358,694 A | 10/1994 | Giovanniello |
| 5,643,558 A | 7/1997 | Provancal |

(Continued)

FOREIGN PATENT DOCUMENTS

| CA | 2445924 | 5/2004 |
| CN | 1796283 A | 7/2006 |

(Continued)

OTHER PUBLICATIONS

Shafran et al., 2005, "A systematic investigation of aluminum ion speciation at high temperature. Part 1. Solution studies", Dalton Transactions, Issue 12:2098-2105.

(Continued)

*Primary Examiner* — Ernst V Arnold
*Assistant Examiner* — Kyung Sook Chang

(57) ABSTRACT

A method of making an antiperspirant active composition and the use of a heating step at elevated temperature to convert $Al_{13}$ polyhydroxyoxoaluminum cations in the species detectable by $^{27}Al$ NMR within an aqueous aluminum salt solution into $Al_{30}$ polyhydroxyoxoaluminum cations in the species detectable by $^{27}Al$ NMR without increasing a SEC Peak 3 area in the SEC chromatogram of the aluminum salt.

17 Claims, 10 Drawing Sheets

(56) References Cited

U.S. PATENT DOCUMENTS

| | | | |
|---|---|---|---|
| 5,705,171 | A | 1/1998 | Iovanni et al. |
| 5,955,065 | A | 9/1999 | Thong et al. |
| 5,997,850 | A | 12/1999 | Tang et al. |
| 6,010,688 | A | 1/2000 | Shen |
| 6,042,816 | A | 3/2000 | Shen |
| 6,066,314 | A | 5/2000 | Tang et al. |
| 6,074,632 | A | 6/2000 | Shen |
| 6,136,302 | A | 10/2000 | Juneja et al. |
| 6,149,897 | A | 11/2000 | Swaile |
| 6,245,325 | B1 | 6/2001 | Shen |
| 6,342,210 | B1 | 1/2002 | Cai et al. |
| 6,375,937 | B1 | 4/2002 | Chopra et al. |
| 6,428,778 | B1 | 8/2002 | Breker et al. |
| 6,436,381 | B1 | 8/2002 | Carrillo et al. |
| 6,451,296 | B1 | 9/2002 | Li et al. |
| 6,682,749 | B1 | 1/2004 | Potechin et al. |
| 6,726,901 | B2 | 4/2004 | Yin et al. |
| 6,835,373 | B2 | 12/2004 | Kolodzik et al. |
| 6,902,724 | B1 | 6/2005 | Parekh et al. |
| 6,936,242 | B2 | 8/2005 | Elliott et al. |
| 6,942,850 | B2 | 9/2005 | Coe et al. |
| 6,969,510 | B2 | 11/2005 | Holerca et al. |
| 7,105,691 | B2 | 9/2006 | Holerca et al. |
| 7,189,387 | B2 | 3/2007 | Chuah et al. |
| 7,229,611 | B2 | 6/2007 | Zamudio-Tena et al. |
| 7,256,875 | B2 | 8/2007 | Maier et al. |
| 2004/0101500 | A1 | 5/2004 | Ashcroft et al. |
| 2004/0265255 | A1 | 12/2004 | Holerca et al. |
| 2005/0265939 | A1 | 12/2005 | Li |
| 2006/0153788 | A1 | 7/2006 | Swaile et al. |
| 2006/0204463 | A1 | 9/2006 | Tang et al. |
| 2006/0292098 | A1 | 12/2006 | Scavone et al. |
| 2007/0003499 | A1 | 1/2007 | Shen et al. |
| 2007/0020211 | A1 | 1/2007 | Li et al. |
| 2007/0110687 | A1 | 5/2007 | Mattai et al. |
| 2007/0196302 | A1 | 8/2007 | Pratt et al. |
| 2007/0196303 | A1 | 8/2007 | Li et al. |
| 2009/0016979 | A1 | 1/2009 | Li et al. |
| 2009/0081117 | A1 | 3/2009 | Deschaume et al. ......... 423/626 |

FOREIGN PATENT DOCUMENTS

| | | |
|---|---|---|
| CN | 101279755 A | 10/2008 |
| EP | 0291334 | 11/1988 |
| GB | 2144992 | 3/1985 |
| WO | WO 2006/046945 | 5/2006 |
| WO | WO 2006/103092 | 10/2006 |
| WO | WO 2007/004163 | 1/2007 |
| WO | WO 2008/063188 | 5/2008 |
| WO | WO 2008/070218 | 6/2008 |
| WO | WO 2009/075678 | 6/2009 |
| WO | WO 2009/076591 | 6/2009 |

OTHER PUBLICATIONS

Rosenberg, Antiperspirant Actives—Enhanced Efficacy Aluminum-Zirconium-Glycine (AZG) Salts, Cosmetics and Toiletries Worldwide, Fondots, D. C. ed., Hertfordshire, UK: Aston Publishing Group, 1993, 252, 254-256.

Allouche et al., 2003, "Conversion of Al13 Keggin e into Al30: a reaction controlled by aluminum monomers," Inorg. Chem. Commun. 6:1167-1170.

Allouche et al., 2000, "Al30: A Giant Aluminum Polycation," Angew Chem. Int. Ed, 39(3):511-514.

Bottero, 1980, "Studies of Hydrolized Aluminum Chloride Solutions, 1. Nature of Aluminum Species and Composition of Aqueous Solutions," The Journal of Physical Chemistry 84:2933-2939.

Casey, 2007, "Reaction Dynamics, Molecular Clusters, and Aqueous Geochemistry," Ann. Rev. Earth Planet Sci. 35:21-46.

Casey, 2006, "Large Aqueous Aluminum Hydroxide Molecules," Chemical Reviews 106(1):1-16.

Chen et al., 2006, "Effect of Thermal Treatment on the Formation and Transformation of Keggin Al13 and Al30 Species in Hydrolytic Polymeric Aluminum Solutions," Colloids & Surfaces A 292(2-3):110-118.

Chen et al., 2006, "Evaluation of $Al_{30}$ Polynuclear Species in Polyaluminum Solutions as Coagulant for Water Treatment," Chemosphere 64(6):912-918.

Chen et al., 2009, "On the Acid-Base Stability of Keggin $Al_{13}$ and $Al_{30}$ Polymers Polyaluminum Coagulants," J. Mater. Sci. 44:3098-3111.

Fu et al., 1991, "Aging Processes of Alumina Sol-Gels: Characterization of New Aluminum Polyoxycations by 27Al NMR Spectroscopy," Chem. Mater. 3:602-610.

Huang et al., 2006, "Separation and Purification of Nano-$Al_{13}$ by UF Method," Colloids and Surfaces A: Physicochem. Eng. Aspects 275:200-208.

International Search Report and Written Opinion in International Application No. PCT/US2010/055030, mailed Sep. 1, 2011.

International Search Report in International Application No. PCT/US2007/087145, mailed Apr. 6, 2009.

International Search Rpeort in International Application No. PCT/US2008/086556, mailed Apr. 6, 2009.

Mertens et al., 2012, "Polyaluminum chloride with high Al30 content as removal agent for arsenic-contaminated well water," Water Research 46:53-62.

Rosenberg, "Antiperspirant Actives—Enhanced Efficacy Aluminum-Zirconium-Glycine (AZG) Salts" (Cosmetics and Toiletries Worldwide, Fondots, D.C. ed., Hartfordshire, UK: Aston Publishing Group, 1993, pp. 252, 254-256).

Roswell et al., 2000, "Speciation and Thermal Transformation in Alumina Sols: Structures of the Polyhydroxyoxoaluminum Cluster [Al30O8(OH)56(H2O)26]18+ and Its δ-Keggin Moiete," J. Amer. Chem. Soc. 122:3777-3778.

Shafran et al., 2004, "High-Temperature Speciation Studies of Al-Ion Hydrolysis," Advanced Engineering Materials 6(10):836-839.

Shafran et al., 2005, "The Static Anion Exchange Method for Generation of High Purity Aluminum Polyoxocations and Monodisperse Aluminum Hydroxide Nanoparticles" J. Mater. Chem. 15(33):3415-3423.

Shen, 1998, "Synthesis and Speciation of Polyaluminum Chloride for Water Treatment," Environment International 24(8):899-910.

U.S. Appl. No. 12/531,145, filed Sep. 14, 2009.

File History from U.S. Appl. No. 12/531,145 through Oct. 20, 2011.

Written Opinion in International Application No. PCT/US2010/055030, mailed Nov. 28, 2012.

Zhang et al., 2008, "Coagulation Characteristics of Polyaluminum Chlorides PAC-Al30 on Humic Acid Removal from Water," Separation & Purification Tech. 63:642-647.

Faust et al., 1998, "Removal of Particulate Matter by Coagulation," Chemistry of Water Treatment, Chapter 6, CRC Press, 2nd ed., pp. 215-270.

International Search Report and Written Opinion in International Application No. PCT/US2011/058559, mailed Apr. 3, 2013.

ANTIPERSPIRANT ACTIVE COMPOSITIONS AND MANUFACTURE THEREOF

This application is a divisional application of application Ser. No. 13/882,488, with a 371 filing date of 29 Apr. 2013, which is a 371 application of Application No. PCT/US2010/55030, filed on 2 Nov. 2010, all of which are incorporated herein by reference.

BACKGROUND

The invention relates to antiperspirant active compositions comprising an aluminum salt and to methods of making an antiperspirant active composition.

Antiperspirant salts, such as aluminum chlorohydrex (also called aluminum chlorohydrex polymeric salts and abbreviated here as "ACH") and aluminum zirconium glycine salts (abbreviated here as "ZAG", "ZAG complexes" or "AZG"), are known to contain a variety of polymeric and oligomeric species with molecular weights (MW) of 100 Da-500,000 Da. It has been clinically shown that, in general, the smaller the species, the higher the efficacy for reducing sweat.

In an attempt to increase the quality and quantity of smaller aluminum and/or zirconium species, a number of efforts have focused on: (1) how to select the components of ACH and ZAG that affect the performance of these materials as antiperspirants; and (2) how to manipulate these components to obtain and/or maintain the presence of smaller types of these components. These attempts have included the development of analytical techniques to identify the components. Size exclusion chromatography ("SEC") or gel permeation chromatography ("GPC") are methods frequently used for obtaining information on polymer distribution in antiperspirant salt solutions. With appropriate chromatographic columns, generally five distinctive groups of polymer species can be detected in commercial ACH and ZAG complexes appearing in a chromatogram as peaks 1, 2, 3, 4 and a peak known as "5, 6", referred to hereinafter as Peak 5. Peak 1 is the larger Zr species (greater than 60 Angstroms). Peaks 2 and 3 are larger aluminum species. Peak 4 is smaller aluminum species (aluminum oligomers, or small aluminum clusters) and has been correlated with enhanced efficacy for both Al and Al/Zr salts. Peak 5 is the smallest aluminum species. Various analytical approaches for characterizing the peaks of ACH and various types of ZAG actives are found in "Antiperspirant Actives—Enhanced Efficacy Aluminum-Zirconium-Glycine (AZG) Salts" by Dr. Allan H. Rosenberg (Cosmetics and Toiletries Worldwide, Fondots, D. C. ed., Hertfordshire, UK: Aston Publishing Group, 1993, pages 252, 254-256).

Attempts to activate antiperspirant salts to produce materials having improved efficacy have included developing processes for obtaining composition having large amounts of Peak 4 species.

The Applicant's earlier WO-A-2009/076591 discloses, inter alia, an antiperspirant composition having a composition with little or no Peak 3 and optionally little or no Peak 5. However, there is still a need for yet further improved antiperspirant compositions.

Solutions of partially neutralized aluminum are known to contain a variety of hydrolytic Al species. The identity and distribution of these various forms depends on the hydrolysis ratio (i.e. the OH:Al molar ratio), the Al precursor and the choice of the reaction condition. In the field of antiperspirant (AP) technology, SEC chromatography is the traditional method used for elucidating the distribution of these Al species. Conventional SEC physically separates Al species into domains which are subsequently measured using a concentration detector. It is generally recognized that at least five domains of Al species can be differentiated by size-exclusive chromatography. These domains are commonly referred to Peak 1, Peak 2 . . . Peak 5, where increasing peak number indicates smaller relative size of the eluting species. As discussed above, Peak 4 and Peak 5 have been implicated as highly efficacious Al domains. Monomeric Al, which is undesirable because of its acidity, is known to elute under Peak 5.

It is well known in the art that such a variety of hydrolytic Al species exists and that it is possible to distinguish large aqueous aluminum hydroxide molecules using spectroscopic methods such as $^{27}$Al NMR which elucidates the structural environment surrounding Al atoms which are embodied in various forms (Casey W H, "Large Aqueous Aluminum Hydroxide Molecules", Chem. Rev. 2006, 106 (1), pages 1 to 16.

There are two regions in a $^{27}$Al NMR spectrum that represent Al nuclei which are octahedrally coordinated (0 ppm-60 ppm) and tetrahedrally coordinated (60 ppm-80 ppm). The octahedral region is exemplified by the hexa-aqua Al species, i.e. monomeric Al, which resonates sharply at 0 ppm. The tetrahedral region is exemplified by resonance at 62.5 ppm from the $Al_{13}$ polyhydroxyoxoaluminum cation. $Al_{13}$ is composed of 12 octahedrally coordinated Al atoms surrounded by one centrally-cited Al atom which is tetrahedrally coordinated. The $Al_{30}$ polyhydroxyoxoaluminum cation is essentially a dimer of the $Al_{13}$ polyhydroxyoxoaluminum cation and contains 2 tetrahedrally sited Al atoms which yield a somewhat broad resonance at 70 ppm.

It is known that $^{27}$Al NMR spectroscopy may not fully elucidate the chemical composition of a partially neutralized Al salt solution, since there are a variety of Al species which give rise to broad, low resolution resonance peaks and thus can be considered as effectively NMR-invisible. Unless the $^{27}$Al NMR spectroscopy is carried out quantitatively, the relative concentration of these NMR-invisible species cannot be determined and must be inferred from SEC chromatography.

The state of the art discloses a number of methods for synthesizing and purifying the $Al_{13}$ polyhydroxyoxoaluminum cation (for example Fu G. et al, "Aging Processes of Alumina Sol-Gels; Characterization of New Aluminum Polycations by $^{27}$Al NMR Spectroscopy" Chem. Mater. 1991, 3(4), pages 602 to 610).

It is known that the $Al_{13}$ polyhydroxyoxoaluminum cation may be converted to obtain the $Al_{30}$ polyhydroxyoxoaluminum cation by heating a solution of the $Al_{13}$ polyhydroxyoxoaluminum cation (Roswell J et al, "Speciation and Thermal Transformation in Alumina Sols; Structures of the Polyhydroxyoxoaluminum Cluster $[Al_{30}O_8(OH)_{56}(H_2O)_{26}]^{18+}$ and its δ-Keggin Moieté", J. Am. Chem. Soc. 2000, 122, pages 3777 to 3778; Chen Z et al, "Effect of thermal treatment on the formation and transformation of Keggin $Al_{13}$ and $Al_{30}$ species in hydrolytic polymeric aluminum solutions", Colloids and Surfaces A: Physiochem. Eng. Aspects, 292 (2007) pages 110 to 118; and Allouche L et al, "Conversion of $Al_{13}$ Keggin ε into $Al_{30}$: a reaction controlled by aluminum monomers", Inorganic Chemistry Communications, 6 (2003) pages 1167-1170).

Heating an $Al_{13}$ solution is the only high-yield synthetic pathway to achieving $Al_{30}$ which has been described in the literature. As well as the references identified above, WO-A-2006/103092 and Shafran K L et al, "The static anion exchange method for generation of high purity aluminum polyoxocations and monodisperse aluminum hydroxide nano-particles", J. Mater. Chem., 2005, 15, pages 3415 to 3423, disclose the use of an ion-exchange process to synthesize $Al_{13}$ to achieve greater than 90% purity, and disclose heating the thus-formed $Al_{13}$ solution to form $Al_{30}$.

However, as discussed above, when synthesizing aluminum salts for use as antiperspirant active compositions, in order to provide enhanced antiperspirant efficacy it is necessary to have a particular peak distribution for the SEC chromatogram of the Al species. The Chen et al paper identified above demonstrates that the concentration of $^{27}Al$ NMR-undetectable Al species, increases dramatically during $Al_{30}$ production. Table 1 below is an extract of data from the Chen et al paper.

Table 1 shows the Al species distribution measured by $^{27}Al$ NMR in hydrolytic polymeric aluminum solutions which were synthesized at 80° C. and then heated at 95° C. for different durations shown.

TABLE 1

Al Species distribution measured by $^{27}Al$ NMR

| Al content (M) | Heating Time | $Al_m$ (%) | $Al_{13}$ (%) | $Al_{30}$ (%) | $Al_u$ (%) |
|---|---|---|---|---|---|
| 0.2M | 24 hr | 5.34 | 6.45 | 73.07 | 15.14 |
| 0.2M | 48 hr | 5.01 | 1.07 | 71.76 | 22.16 |
| 0.5M | 24 hr | 4.65 | 1.16 | 35.12 | 59.07 |
| 0.5M | 48 hr | 4.86 | 1.27 | 38.48 | 55.39 |
| 1.0M | 24 hr | 8.38 | 0.72 | 14.73 | 76.17 |
| 1.0M | 48 hr | 8.11 | 0.21 | 16.02 | 75.66 |

For different molar Al contents of 0.2M, 0.5M and 1.0M, it may be seen from table 1 that for each 24 hour heating time sample the $Al_{30}$ proportion in the Al species was at most less than 75% and that increasing the heating time to 48 hours does not significantly increase, or even reduces, the $Al_{30}$ species while potentially increasing the $Al_u$ NMR-inactive Al species. Therefore the data published by Chen et al shows that prolonged heating of an $Al_{13}$ solution with the aim of trying to synthesize $Al_{30}$ may result in unacceptably low $Al_{30}$ concentrations and, importantly for aluminum antiperspirant actives, produce NMR-inactive Al species that may elute under Peak 2 or Peak 3 and reduce antiperspirant efficacy.

There is a need in the art for aluminum antiperspirant actives which have high antiperspirant efficacy.

There is also a need in the art for aluminum antiperspirant actives which have high stability.

There is also a need in the art for aluminum antiperspirant actives which have the combination of high antiperspirant efficacy and high stability.

BRIEF SUMMARY

The present invention is at least partly predicated on the finding by the present inventors that any pathway involving the prolonged heating of a partially neutralized Al solution inevitably results in the significant formation of NMR-invisible Peak 2 or Peak 3 species. In other words, when considering the requirements for an antiperspirant active composition, in order to provide Al species which have high antiperspirant efficacy, it is necessary to consider not only the nature and proportion of Al species which are determinable by $^{27}Al$ NMR spectroscopy, but also to consider the nature and proportion of NMR-invisible species which may be present as Peak 2 or Peak 3 species which would reduce antiperspirant efficacy.

The $Al_{30}$ polyhydroxyoxoaluminum cation is more stable than the $Al_{13}$ polyhydroxyoxoaluminum cation, and both the $Al_{30}$ and $Al_{13}$ polyhydroxyoxoaluminum cations elute under SEC Peak 4, and so have high antiperspirant efficacy. Accordingly, the present invention is predicated on the finding that an antiperspirant salt can be produced containing primarily $Al_{30}$ in the Al species, so as to provide a highly stable antiperspirant active, and with high antiperspirant efficacy because of high Peak 4 area, but low, or negligible, or even entirely absent, Peak 3 area. The present inventors believe that no current methods exist in the art to synthesize the efficacious and stable $Al_{30}$ polyhydroxyoxoaluminum cation without forming significant amounts of large Al species which would elute under SEC Peak 3 and therefore reduce antiperspirant efficacy.

The present inventors have devised an antiperspirant active composition which has high antiperspirant efficacy and stability, and a method of manufacture thereof, and in particular synthesize the efficacious and stable $Al_{30}$ polyhydroxyoxoaluminum cation without forming significant amounts of large Al species which would elute under SEC Peak 3 and therefore reduce antiperspirant efficacy.

The present invention accordingly provides an antiperspirant active composition comprising an aluminum salt, the aluminum salt (i) having an aluminum to chloride molar ratio of 0.3:1 to 3:1; (ii) exhibiting an $^{27}Al$ NMR spectrum with a species distribution including at least 90% $Al_{30}$ polyhydroxyoxoaluminum cation as the predominant species detectable by $^{27}Al$ NMR within the aluminum salt. Optionally, the aluminum salt exhibits a SEC chromatogram having a SEC Peak 4 area of at least 90% of a total area of Peaks 1, 2, 3, 4 and 5 in the SEC chromatogram.

In this specification, the SEC chromatogram is measured using an aqueous solution of the aluminum salt.

In some embodiments, the $^{27}Al$ NMR spectrum has a species distribution including at least 95% $Al_{30}$ polyhydroxyoxoaluminum cation as the predominant species detectable by $^{27}Al$ NMR within the aluminum salt.

In some embodiments, the $^{27}Al$ NMR spectrum has a species distribution including at most 5% $Al_{13}$ polyhydroxyoxoaluminum cation in the species detectable by $^{27}Al$ NMR within the aluminum salt. In some embodiments, the $^{27}Al$ NMR spectrum has a species distribution including no $Al_{13}$ polyhydroxyoxoaluminum cation in the species detectable by $^{27}Al$ NMR within the aluminum salt. In some embodiments, the $^{27}Al$ NMR spectrum has a species distribution including at most 5% $Al_m$, $Al_m$ comprising an aluminum- and chloride-containing monomer, in the species detectable by $^{27}Al$ NMR within the aluminum salt.

In some embodiments, the aluminum salt has an OH to Al ratio of at most 2.6:1, and in other embodiments 2:1 to 2.6:1, optionally an OH to Al ratio of 2:1 to 2.5:1, or 2.3:1 to 2.5:1.

The antiperspirant active composition may optionally further comprise a buffer, wherein a molar ratio of buffer to aluminum is at least 0.1:1. In other embodiments, the molar ratio is 0.1:1 to 3:1. The buffer may be at least one buffer chosen from an amino acid and betaine. Optionally, the buffer is an amino acid and a molar ratio of amino acid to aluminum is at least 0.1:1. In some embodiments, the amino acid is glycine.

In some embodiments, the composition has a SEC Peak 4 area of at least 95% of a total area of Peaks 1, 2, 3, 4 and 5 in the SEC chromatogram. In some embodiments, the composition has a SEC Peak 3 area of less than 5% of a total area of Peaks 1, 2, 3, 4 and 5 in the SEC chromatogram, and most preferably has no SEC Peak 3 area in the SEC chromatogram.

In some embodiments, the composition has a SEC Peak 5 area of less than 5% of a total area of Peaks 1, 2, 3, 4 and 5 in the SEC chromatogram, and most preferably has no SEC Peak 5 area in the SEC chromatogram.

In some embodiments, the antiperspirant active composition has a SEC Peak 4 area of 95 to 100%, no SEC Peak 3 area, and a SEC Peak 5 area of from 0 to 5% of a total area of Peaks 1, 2, 3, 4 and 5 in the SEC chromatogram.

The antiperspirant active composition may further comprise zirconium, and optionally a molar ratio of aluminum to zirconium is 5:1 to 10:1.

The present invention also provides a method of making an antiperspirant active composition comprising:

I) heating an aqueous solution containing a first aluminum salt having an aluminum to chloride molar ratio of 0.3:1 to 3:1 and a buffer, wherein the buffer is an amino acid or betaine and a molar ratio of buffer to aluminum is at least 0.1:1, at a temperature of 50° C. to 100° C. for a period of time of 1 hour to 6 hours to obtain a first aluminum salt solution;

II) adding to the first aluminum salt solution an aqueous solution of an inorganic base to obtain a second pH adjusted aluminum salt solution having an OH:Al molar ratio of at most 2.6:1 and a pH of 2 to 5;

III) heating the second pH adjusted aluminum salt solution at a temperature of 50° C. to 100° C. for a period of time of at least 6 hours or, in other embodiments, at least 12 hours to obtain a third aluminum salt solution containing a third aluminum salt exhibiting an $^{27}$Al NMR spectrum with a species distribution including at least 90% $Al_{30}$ polyhydroxyoxoaluminum cation as the predominant species detectable by $^{27}$Al NMR within the third aluminum salt; and, optionally, exhibiting a SEC chromatogram having a SEC Peak 4 area of at least 90% of a total area of Peaks 1, 2, 3, 4 and 5 in the SEC chromatogram; and IV) optionally adding an aqueous solution containing a zirconium compound to the second pH adjusted aluminum salt solution to thereby obtain a second pH adjusted aluminum-zirconium salt solution having a molar ratio of aluminum to zirconium of 5:1 to 10:1.

In some embodiments, the buffer is glycine. In some embodiments, the inorganic base includes at least one member chosen from calcium hydroxide, strontium hydroxide, barium hydroxide, calcium oxide, strontium oxide, barium oxide, calcium carbonate, strontium carbonate, barium carbonate, yttrium hydroxide, yttrium oxide, and yttrium carbonate. Typically, the inorganic base is calcium hydroxide. In some embodiments, the second pH adjusted aluminum salt solution has an OH to Al molar ratio of 2.0:1 to 2.5:1 or 2.1:1 to 2.5:1.

In some embodiments, the first aluminum salt is an aluminum chloride compound chosen from aluminum trichloride, aluminum chlorohexahydrate, and aluminum dichlorohydrate. Optionally, the composition further comprises zirconium and step IV) is present in the method. The zirconium compound may be $ZrOC_2 \cdot 8H_2O$.

In some embodiments, the $^{27}$Al NMR spectrum has a species distribution including at least 95% $Al_{30}$ polyhydroxyoxoaluminum cation as the predominant species detectable by $^{27}$Al NMR within the third aluminum salt. In some embodiments, the $^{27}$Al NMR spectrum has a species distribution including at most 5% $Al_{13}$ polyhydroxyoxoaluminum cation in the species detectable by $^{27}$Al NMR within the third aluminum salt, and preferably the $^{27}$Al NMR spectrum has a species distribution including no $Al_{13}$ polyhydroxyoxoaluminum cation in the species detectable by $^{27}$Al NMR within the third aluminum salt. In some embodiments, the $^{27}$Al NMR spectrum has a species distribution including at most 5% $Al_m$, $Al_m$ comprising an aluminum- and chloride-containing monomer, in the species detectable by $^{27}$Al NMR within the third aluminum salt.

In some embodiments, the third aluminum salt has a SEC Peak 4 area of at least 95% of a total area of Peaks 1, 2, 3, 4 and 5 in the SEC chromatogram. In some embodiments, the third aluminum salt has a SEC Peak 3 area of less than 5% of a total area of Peaks 1, 2, 3, 4 and 5 in the SEC chromatogram, and preferably the third aluminum salt has no SEC Peak 3 area in the SEC chromatogram. In some embodiments, the third aluminum salt has a SEC Peak 5 area of less than 5% of a total area of Peaks 1, 2, 3, 4 and 5 in the SEC chromatogram.

In some embodiments, in step III) the period of time is at least 12 hours, or in some embodiments at least 24 hours.

The present invention further provides the use of a heating step at elevated temperature to convert $Al_{13}$ polyhydroxyoxoaluminum cations in the species detectable by $^{27}$Al NMR within an aqueous aluminum salt solution into $Al_{30}$ polyhydroxyoxoaluminum cations in the species detectable by $^{27}$Al NMR without increasing a SEC Peak 3 area in the SEC chromatogram of the aluminum salt, the aqueous aluminum salt solution having an aluminum to chloride molar ratio of 0.3:1 to 3:1; a buffer, wherein the buffer is an amino acid or betaine and a molar ratio of buffer to aluminum is at least 0.1:1; an OH:Al molar ratio of at most 2.6:1; and a pH of 2 to 5; and the heating step comprises heating the aqueous aluminum salt solution at a temperature of 50° C. to 100° C. for a period of time of at least 3 hours, or in other embodiment at least 12 hours.

In some embodiments, the heating step converts all the $Al_{13}$ polyhydroxyoxoaluminum cation species present in the aqueous aluminum salt solution into the $Al_{30}$ polyhydroxyoxoaluminum cation species. In some embodiments, the heating step reduces a SEC Peak 5 area in the SEC chromatogram. Optionally, the period of time is at least 12 hours or, in other embodiments, at least 24 hours. In some embodiments, the buffer is glycine.

In some embodiments, the OH:Al molar ratio has been achieved by adding to the aqueous aluminum salt solution an inorganic base including at least one member chosen from calcium hydroxide, strontium hydroxide, barium hydroxide, calcium oxide, strontium oxide, barium oxide, calcium carbonate, strontium carbonate, barium carbonate, yttrium hydroxide, yttrium oxide, and yttrium carbonate. Typically, the inorganic base is calcium hydroxide. Optionally, the OH to Al molar ratio is 2.0:1 to 2.5:1 or 2.1:1 to 2.5:1.

In some embodiments, the aluminum salt is an aluminum chloride compound chosen from aluminum trichloride, aluminum chlorohexahydrate, and aluminum dichlorohydrate.

In some embodiments, the heating increases the $Al_{30}$ polyhydroxyoxoaluminum cation species in the $^{27}$Al NMR spectrum from at least 90% to at least 95% of the species detectable by $^{27}$Al NMR within the aluminum salt.

In some embodiments, after the heating step the aluminum salt has a SEC Peak 4 area of at least 95% of a total area of Peaks 1, 2, 3, 4 and 5 in the SEC chromatogram. In some embodiments, after the heating step the aluminum salt has a SEC Peak 3 area of less than 5% of a total area of Peaks 1, 2, 3, 4 and 5 in the SEC chromatogram, and preferably has no SEC Peak 3 area in the SEC chromatogram. In some embodiments, after the heating step the aluminum salt has a SEC Peak 5 area of less than 5% of a total area of Peaks 1, 2, 3, 4 and 5 in the SEC chromatogram.

The present invention also provides the use, for enhancing the stability of an aluminum salt of an antiperspirant active composition without increasing a SEC Peak 3 area in the SEC chromatogram of the aluminum salt, of heating, at a temperature of 50° C. to 100° C. for a period of time of at least 6 hours or, in other embodiments, at least 12 hours, an aqueous solution of the aluminum salt having an aluminum to chloride molar ratio of 0.3:1 to 3:1; a buffer, the buffer being an amino acid or betaine and a molar ratio of buffer to aluminum being at least 0.1:1; an OH:Al molar ratio of at most 2.6:1; and a pH of 2 to 5.

The present invention further provides an antiperspirant active composition including an aluminum salt produced by the method of the invention or the use of the invention.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

DETAILED DESCRIPTION

Figure 1:
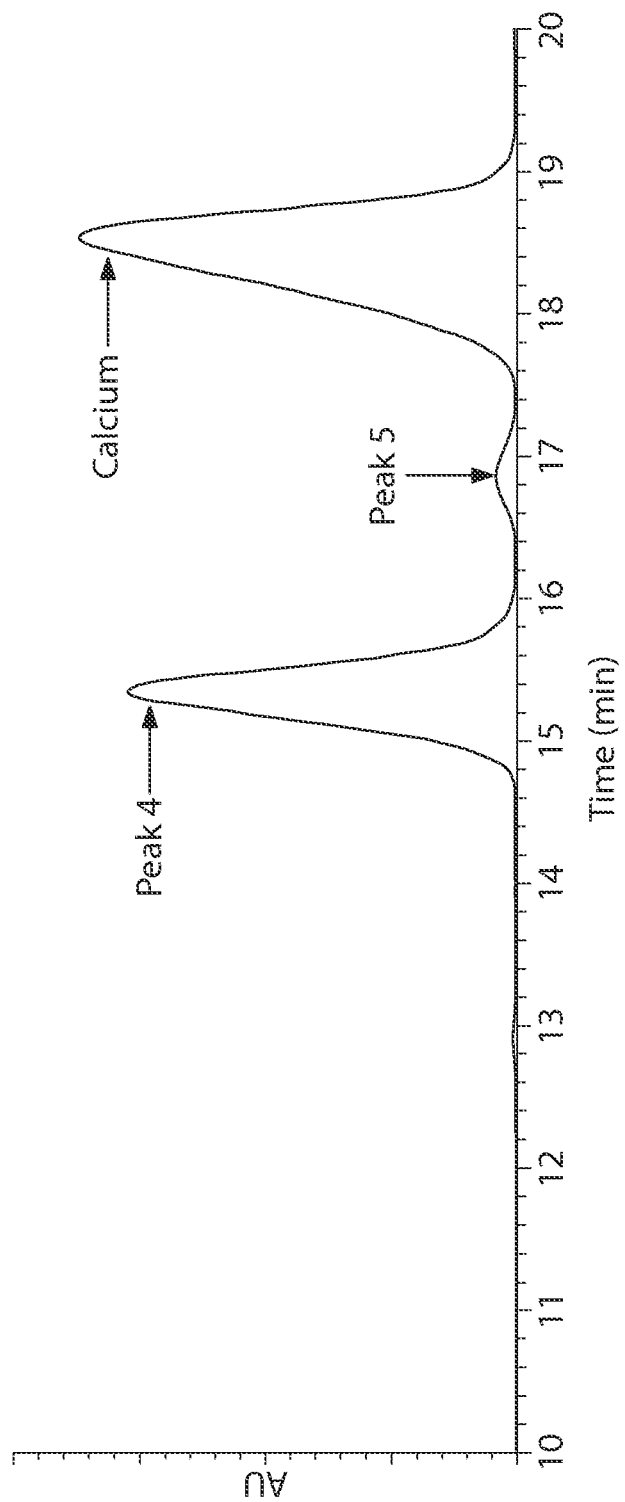
FIG. 1 illustrates an SEC chromatogram of an aluminum salt produced according to Example 1 of the present invention

As used throughout, ranges are used as a shorthand for describing each and every value that is within the range. Any value within the range can be selected as the terminus of the range.

The present invention is directed to an antiperspirant active composition having a high SEC peak 4 in aqueous solution. The composition is obtained by a stepwise procedure to neutralize aluminum chloride in a solution (optionally buffered) using inorganic bases. In some embodiments, the antiperspirant active compositions obtained by this stepwise procedure include aluminum salts having an aluminum to chloride molar ratio of 0.3:1 to 3:1, optionally, the aluminum salt exhibits a SEC chromatogram having a SEC Peak 4 area of at least 90% of a total area of Peaks 1, 2, 3, 4 and 5 in the SEC chromatogram in aqueous solution. The composition may optionally include zirconium.

The compositions may be made in a variety of ways involving a stepwise procedure to neutralize aluminum chloride in solution (optionally buffered) using inorganic basic salts. The procedure generally includes the step of heating an aqueous solution containing an aluminum chloride compound (optionally with a buffer agent) at a temperature of 50° C. to 100° C., optionally 50° C. to 95° C., for a period of time of 1 hour to 6 hours. The heating may be under stirring, such as vigorous stirring, or under reflux. In one such embodiment, an aqueous solution containing an aluminum chloride compound and a buffer agent is heated at a temperature of 75° C. to 95° C. to reflux for a period of time of 2 hours to 4 hours. In one embodiment, the temperature is 95° C. under vigorous stirring for a period of time of 2.5 hours.

To adjust the pH of the aluminum salt solution, an aqueous solution of an inorganic base is added to the heated solution to thereby obtain a pH adjusted aluminum salt solution having a hydroxide to aluminum molar ratio of 1:1 to 4:1, and a pH of 2 to 5. In one such embodiment, the hydroxide to aluminum molar ratio of 2:1 to 3:1. In another such embodiment, the hydroxide to aluminum molar ratio is 2.1:1 to 2.6:1.

In one embodiment, the inorganic base can be at least one base chosen from metal hydroxides, calcium hydroxide, strontium hydroxide, sodium hydroxide, barium hydroxide, metal oxides, calcium oxide, strontium oxide, barium oxide, metal carbonates, calcium carbonate, strontium carbonate, barium carbonate, yttrium hydroxide, yttrium oxide, and yttrium carbonate.

Optionally, a buffer can be included. Buffers that can be used can be chosen from amino acids, such as glycine, and betaine, such as betaine monohydrate. The buffer to aluminum molar ratio in certain embodiments can be at least 0.1:1, or 0.1:1 to 3:1. In another embodiment, the buffer to aluminum molar ratio is 0.1:1 to 2:1.

In one embodiment, the inorganic base is calcium hydroxide. In one such embodiment, the addition of calcium hydroxide provides an aqueous solution having a Ca(OH)$_2$: glycine molar ratio of at least 0.1:1.

When a buffer is absent, significant Peak 3 species in the SEC chromatogram begin to form when the total Al concentration is above 0.2M. When a buffer is present, the total Al concentration can reach up to 2.5M while maintaining a predominant Peak 4 in the SEC chromatogram. In one embodiment, an aqueous aluminum chloride salt solution is buffered with glycine and held at 50° C. to 95° C. under vigorous stirring for a period time of 1 to 6 hours. To the heated solution, an aqueous solution of an inorganic base is added dropwise over a period of time of 1 to 3 hours while maintaining the aluminum-glycine solution at 50° C. to 95° C. under vigorous stirring. In one such embodiment, the solution has a glycine to aluminum molar ratio of 1.5. In another such embodiment, the solution has a glycine to aluminum molar ratio of 0.5.

In some embodiments, a zirconium salt may also be added to the pH adjusted aluminum salt solution. In one other such embodiment, the molar ratio of Al:Zr is 5:1 to 10:1. The zirconium salt may be ZrOCl$_2$.8H$_2$O. In one such embodiment, the molar ratio of Al:Zr is 8. In another such embodiment, the molar ratio of Al:Zr is 7. In one other such embodiment, the molar ratio of Al:Zr is 9.

For the above methods, the aluminum chloride salt and inorganic base may be obtained from a variety of sources. In one embodiment, the aluminum chloride salt includes aluminum trichloride, aluminum chlorohexahydrate and aluminum dichlorohydrate. In one such embodiment, the aluminum chloride salt is aluminum chlorohexahydrate.

The present invention provides for aluminum antiperspirant active compositions and/or aluminum-zirconium antiperspirant active compositions having high levels of low molecular weight Al and Zr species. As illustrated in FIG. 1, for example, the high levels of low molecular weight Al and Zr species is reflected in a SEC trace that has an intense Peak 4, low Peaks 1, 2, 3 and 5. The polymerization of the antiperspirant actives in aqueous solutions and the correspondent gelation process were followed by monitoring the molecular weight profile of the polyoxohalides in time by SEC. The relative retention time ("Kd") for each of these peaks varies depending on the experimental conditions, but the peaks remain relative to each other. The SEC data for the examples was obtained using an SEC chromatogram using the following parameters: Waters® 600 analytical pump and controller, Rheodyne® 77251 injector, Protein-Pak® 125 (Waters) column, Waters 2414 Refractive Index Detector. 5.56 mM nitric acid mobile phase, 0.50 ml/min flow rate, 2.0 microliter injection volume. Data was analyzed using Water® Empower software (Waters Corporation, Milford, Mass.). The concentration of the antiperspirant in aqueous solution does not affect the retention time in the machine.

The design of modern antiperspirant (AP) salts aims at actives with high levels of low molecular weight Al and Zr species, which is reflected in a SEC trace that has intense Peak 4 and low Peaks 1, 2, and 3, and optionally low Peak 5. Throughout the present study, the levels of the species corresponding to these peaks are estimated based on the following ratios (or percentages):

$$f_{Pi} = \frac{Pi}{\Sigma Pj} i = 1, 2, 3, 4, 5; j = 2, 3, 4, 5$$

where $f_{Pi}$ is the fraction of peak i, and Pi or Pj are the intensity of peaks Pi or Pj, respectively. The amount of low molecular weight Al species will be correlated with the fraction, $f_{P4}$, or percentage, $f_{P4} \times 100$, of SEC-Peak 4. In brief, a preferred antiperspirant salt would have a very low $f_{P1}$, $f_{P2}$, $f_{P3}$, and/or $f_{P5}$, and a high $f_{P4}$.

In certain embodiments, the ratio of Peak 4 to Peak 3 is at least 8, 9, 10, 11, 12, 13, 14, 15, 16, 17, 18, 19, 20, 25, 30, 35, 40, 45, 50, 60, 70, 80, 90, 100, or any number up to infinity. Preferably, Peak 3 is so low as to be undetectable.

In one embodiment, an aluminum salt and/or aluminum-zirconium salt, in aqueous solution, exhibit a SEC profile wherein the SEC Peak 4 to Peak 3 intensity ratio is even as high as infinity, because the Peak 3 is undetectable. In some embodiments, the percentage of SEC Peak 4 of a total area of Peaks 1, 2, 3, 4 and 5 in the SEC chromatogram is: at least at least 90%; at least 95%, or 95 to 100%. In another such embodiment, the SEC Peak 4 area is 100%.

In another embodiment, the aluminum salt and/or the aluminum-zirconium salt, in aqueous solution, exhibits a SEC profile which exhibits low percentage of SEC Peak 3. In such embodiments, the composition has the percentage of SEC Peak 3 area of a total area of Peaks 1, 2, 3, 4 and 5 in the SEC chromatogram is: less than 5%; less than 2%; less than 1%; less than 0.9%; less than 0.8%; less than 0.7%; less than 0.6%; of less than 0.5%; less than 0.4%; less than 0.3%; less than 0.2%; or less than 0.1%. In another such embodiment, the composition has no SEC Peak 3 area.

In another embodiment, the aluminum salt and/or the aluminum-zirconium salt, in aqueous solution, exhibits a SEC profile which exhibits low percentages of SEC Peak 5. In such embodiments, the percentage of SEC Peak 5 area of a total area of Peaks 1, 2, 3, 4 and 5 in the SEC chromatogram is: less than 5%; or less than 1%. In another such embodiment, the composition has no SEC Peak 5 area.

In other embodiments, the aluminum salt and/or the aluminum-zirconium salt, in aqueous solution, exhibits a SEC profile which exhibits a low percentage of SEC Peak 1 and a low percentage of SEC Peak 2. In such embodiments, the percentage of SEC Peak 1 area of a total area of Peaks 1, 2, 3, 4 and 5 in the SEC chromatogram is less than 5%; less than 2%; or less than 1%, or the salt has no SEC Peak 1 area. In other embodiments, the percentage of SEC Peak 2 area of a total area of Peaks 1, 2, 3, 4 and 5 in the SEC chromatogram is less than 5%; less than 2% or less than 1%; or the salt has no SEC Peak 2 area. Preferably, the salt has no Peak 1 area and no Peak 2 area. More preferably, the salt has no Peak 1 area, no Peak 2 area and no Peak 3 area. Yet more preferably, the salt has no Peak 1 area, no Peak 2 area, no Peak 3 area and no Peak 5 area.

The aluminum antiperspirant active compositions and/or aluminum-zirconium antiperspirant active compositions may be used in a variety of antiperspirant products. If the product is used as a solid powder, the size of the particles of antiperspirant active of the invention can be any desired size, and may include conventional sizes such as in the range of 2 to 100 microns, with selected grades having an average particle size of 30-40 microns; finer sized grades having an average particle size distribution of 2-10 microns with an average size of 7 microns as made by a suitable dry-grinding method; and micronized grades having an average particle size of less than or equal to 2 microns, or less than or equal to 1.5 microns.

The compositions of this invention may be used to formulate antiperspirants having improved efficacy. Such antiperspirants include solids such as sticks and creams (creams sometimes being included in the term "soft solid"), gels, liquids (such as are suitable for roll-on products), and aerosols. The forms of these products may be suspensions or emulsions. These antiperspirant actives can be used as the antiperspirant active in any antiperspirant composition.

Examples of Suitable Formulations

Sticks

Stick products may be made with conventional gelling agents such as stearyl alcohol and dibenzylidene sorbitol. A sample formulation is as follows:

40-55% (particularly 45%);
cyclomethicone (especially D5 cyclomethicone);
20-30% (particularly 21%);
stearyl alcohol 7-15% (particularly 10%);
talc 15-22% (particularly 22%);
antiperspirant active of the invention in particle form; and
1-3% (particularly 2%) fragrance.

Roll Ons

Roll Ons having a sample formulation:
45-65% (particularly 55%) cyclomethicone (especially D5 cyclomethicone);
0.1-10% (particularly 3%) cyclomethicone/dimethicone copolyol (such as Dow Corning 2-5185C) 10-25% (particularly 20%);
antiperspirant active of the invention in solution form (25-45% actives on an anhydrous basis in water);
5-30% (particularly 20%) water; and
1-3% (particularly 2%) fragrance.

Soft Solids

Soft solids may be made with formulations described in U.S. Pat. No. 6,682,749. A sample formulation is as follows:
- 40-70% (particularly 50%) elastomer in cyclomethicone (KSG-15 from Shin-Etsu);
- 5-15% (particularly 6%) polyethylene (for example, beads having a density in the range of 0.91-0.98 g/cm; and an average particle size in the range of 5-40 microns);
- 10-20% (particularly 15%) C12-15 alkylbenzoate (FIN-SOLV™ TN from Finetex);
- 0.1-25%% (particularly 22%) antiperspirant active of the invention in powder form;
- 1-15% (particularly 5%) dimethicone (particularly with a viscosity of 100 centistokes); and
- 1-3% (particularly 2%) fragrance.

Gels

Gels may be made with a variety of formulations such as:
- 5-50% (particularly 29%) cyclomethicone (particularly D5);
- 0.1-10% (particularly 3%) cyclomethicone/dimethicone copolyol (such as Dow Corning 2-5185C);
- 0-10% (particularly 5%) hydrogenated polyisobutene 250;
- 0-10% (particularly 5%) C12-15 alkylbenzoate (FIN-SOLV™ TN from Finetex);
- 0-10% (particularly 5%) dimethicone (particularly with a viscosity of 100 centistokes);
- 0.1-25% (particularly 20%) antiperspirant active of the invention in powder form or 10-25% (particularly 20%) of active in solution (25-45% actives on an anhydrous basis);
- 5-50% (particularly 30%) water, and
- 1-3% (particularly 2%) fragrance.

Note that in the explanation of the invention, where water is listed it is intended to count the contribution of the water present in the antiperspirant solution as part of the overall water content. Thus, water is sometimes listed as part of the actives solution or sometimes listed separately.

In one embodiment the refractive indices of the external and internal phases are matched within 0.005 to obtain a clear product.

Other Formulations of Interest

Formulation A
- 0.5-2.5% dimethicone copolyol (for example, Dow Corning 2-5185 C (48%));
- 55-65% elastomer in cyclomethicone (for example, DC-9040 from Dow Corning Corporation (Midland, Mich.) or KSG-15 from Shin-Etsu Silicones of America (Akron, Ohio));
- 1-10% PPG-3 myristyl ether;
- 10-25% antiperspirant active of the invention;
- 10-25% water; and
- 0.5-1.5% fragrance.

Formulation B
- 1.0-3.0% dimethicone copolyol (for example, Dow Corning 2-5185C (48%))
- 40-60% elastomer in cyclomethicone (for example, DC-9040 from Dow Corning Corporation (Midland, Mich.) or KSG-15 from Shin-Etsu Silicones of America (Akron, Ohio));
- 1-5% cyclomethicone (in addition to that found in the elastomer);
- 4-12% PPG-3 myristyl ether;
- 15-30% antiperspirant active of the invention;
- 15-35% water; and
- 0.5-1.5% fragrance.

Formulation C
- 1.0-3.0% dimethicone copolyol (for example, Dow Corning 2-5185 C (48%));
- 1-10% hydrogenated polyisobutene (for example, Fancol™. Polyiso 250);
- 40-55% elastomer in cyclomethicone (for example, DC-9040 from Dow Corning Corporation (Midland, Mich.) or KSG-15 from Shin-Etsu Silicones of America (Akron, Ohio));
- 3-8% PPG-3 myristyl ether;
- 15-20% antiperspirant active of the invention;
- 20-30% water; and
- 1.0-3.0% fragrance.

Formulation D
- 1.0-3.0% dimethicone copolyol (for example, Dow Corning 2-5185 C (48%));
- 40-60% elastomer in cyclomethicone (for example, DC-9040 from Dow Corning Corporation (Midland, Mich.) or KSG-15 from Shin-Etsu Silicones of America (Akron, Ohio));
- 3-8% PPG-3 myristyl ether;
- 15-30% antiperspirant active of the invention;
- 15-30% water;
- 0.5-1.5% fragrance; and
- 1-10% diethylhexyl naphthalate Formulation E
- 0.5-2.5% dimethicone copolyol (for example, Dow Corning 2-5185C (48%));
- 60-70% elastomer in cyclomethicone (for example, DC-9040 from Dow Corning Corporation (Midland, Mich.) or KSG-15 from Shin-Etsu Silicones of America (Akron, Ohio));
- 7-10% antiperspirant active of the invention;
- 25-35% water;
- 1-10% methylpropylene diol (MPDiol); and
- 0.5-1.5% fragrance Formulation F
- 1.0-3.0% dimethicone copolyol (for example, Dow Corning 2-5185 C (48%));
- 6-10% hydrogenated polyisobutene (for example, FANCOL™ Polyiso 250);
- 35-45% elastomer in cyclomethicone (for example, DC-9040 from Dow Corning Corporation (Midland, Mich.) or KSG-15 from Shin-Etsu Silicones of America (Akron, Ohio));
- 6-10% PPG-3 myristyl ether;
- 40-50% antiperspirant active of the invention as 43% active in water no additional water; and
- 0.5-1.0% fragrance.

Formulation G
- 0.1-0.6% dimethicone copolyol (for example, Dow Corning 2-5185 C (48%));
- 4-7% hydrogenated polyisobutene (for example, FANCOL™ Polyiso 250);
- 40-50% elastomer in cyclomethicone (for example, DC-9040 from Dow Corning Corporation (Midland, Mich.) or KSG-15 from Shin-Etsu Silicones of America (Akron, Ohio));
- 4-7% PPG-3 myristyl ether;
- 40-50% antiperspirant active of the invention as 43% active in water no additional water; and
- 0.5-1.0% fragrance.

Formulation H
- 0.5-2.0% dimethicone copolyol (for example, Dow Corning 2-5185 C (48%));

1-7% hydrogenated polyisobutene (for example, FANCOL™ Polyiso 250);

40-50% elastomer in cyclomethicone (for example, DC-9040 from Dow Corning Corporation (Midland, Mich.) or KSG-15 from Shin-Etsu Silicones of America (Akron, Ohio));

45-55% antiperspirant active as 43% active of the invention in water no additional water; and 0.5-1.5% fragrance.

Formulation I 2-7% dimethicone copolyol (for example, Dow Corning 2-5185 C (48%));

0.1-1% Oleath-20 1-5% C12-15 alkyl benzoate (FINSOLV™ TN);

15-25% elastomer in cyclomethicone (for example, DC-9040 from Dow Corning Corporation (Midland. Mich.) or KSG-15 from Shin-Etsu Silicones of America (Akron, Ohio));

15-25% antiperspirant active of the present invention;

15-30% water; and 0.5-1.5% fragrance

The cosmetic composition incorporating the antiperspirant salt according to the present invention can be packaged in conventional containers, using conventional techniques. Where a gel, cream or soft-solid cosmetic composition is produced, the composition can be introduced into a dispensing package (for example, conventional packages for gels with glide on applicators, jars where the gel or cream is applied by hand, and newer style packages having a top surface with pores) as conventionally done in the art. Thereafter, the product can be dispensed from the dispensing package as conventionally done in the art, to deposit the active material, for example, on the skin. For sticks, sprays, aerosols and roll-ons the compositions can be placed in conventional types of container (with the inclusion of propellants in aerosols). This provides good deposition of the active material on the skin.

Compositions of the present invention can be formulated as clear, translucent or opaque products. A desired feature of the present invention is that a clear, or transparent, cosmetic composition, (for example, a clear or transparent deodorant or antiperspirant composition) can be provided. The term clear or transparent according to the present invention is intended to connote its usual dictionary definition; thus, a clear liquid or gel antiperspirant composition of the present invention allows ready viewing of objects behind it. By contrast, a translucent composition, although allowing light to pass through, causes the light to be scattered so that it will be impossible to see clearly objects behind the translucent composition. An opaque composition does not allow light to pass there through. Within the context of the present invention, a gel or stick is deemed to be transparent or clear if the maximum transmittance of light of any wavelength in the range 400-800 nm through a sample 1 cm thick is at least 35%, or at least 50%. The gel or liquid is deemed translucent if the maximum transmittance of such light through the sample is between 2% and less than 35%. A gel or liquid is deemed opaque if the maximum transmittance of light is less than 2%. The transmittance can be measured by placing a sample of the aforementioned thickness into a light beam of a spectrophotometer whose working range includes the visible spectrum, such as a Bausch & Lomb Spectronic 88 Spectrophotometer. As to this definition of clear, see EP-A-0291334. Thus, according to the present invention, there are differences between transparent (clear), translucent and opaque compositions.

The present invention is exemplified by the following non-limiting Examples.

EXAMPLES

Example 1

An aqueous solution of 0.5M $AlCl_3.6H_2O$ (50 mmol) was buffered with 1.23M glycine (123 mmol) and heated to 95° C. under vigorous stirring. To this solution, a 1 N $Ca(OH)_2$ (61.5 mmol) was added dropwise over a 2 hour 30 minute period until a final molar ratio of OH:Al of 2.46 was achieved. The pH after the reaction was 3.8. A 50 ml aliquot was removed and subjected to testing by SEC chromatography and $^{27}Al$ NMR spectroscopy.

In this specification, the use of $^{27}Al$ NMR data is not quantitative but considers only NMR-visible Al species and in particular resonances at 0 ppm, 62.5 ppm and 70 ppm. When calculating the relative amounts of Al embodied in the $Al_{13}$ and $Al_{30}$ polyhydroxyoxoaluminum cations, the tetrahedral resonance peak is integrated and must be multiplied by a scaling factor to account for other octahedrally coordinated Al present in the structure. For example, the resonance from the $Al_{13}$ polyhydroxyoxoaluminum cation must be multiplied by 13 whereas the resonance from the $Al_{30}$ polyhydroxyoxoaluminum cation must be multiplied by 15. Also, the NMR data do not indicate the amount of undetected Al embodied in NMR-invisible species. However, the NMR values discussed in the Examples serve as meaningful guidelines as to the chemical composition of the buffered Al salts directly measurable by $^{27}Al$ NMR spectroscopy.

As illustrated in FIG. 1, the SEC chromatogram shows exclusively SEC-Peak 4 and SEC-Peak 5, which are known to represent active antiperspirant species. No SEC-Peak 3 species is observed. No SEC-Peak 1 species or SEC-Peak 2 species is observed. The SEC-Peak 4 area comprised 95.5%, i.e. at least 90%, of the total area of Peaks 1, 2, 3, 4 and 5 in the SEC chromatogram. The SEC-Peak 5 area comprised 4.5%, i.e. less than 5%, of the total area of Peaks 1, 2, 3, 4 and 5 in the SEC chromatogram.

Figure 2:
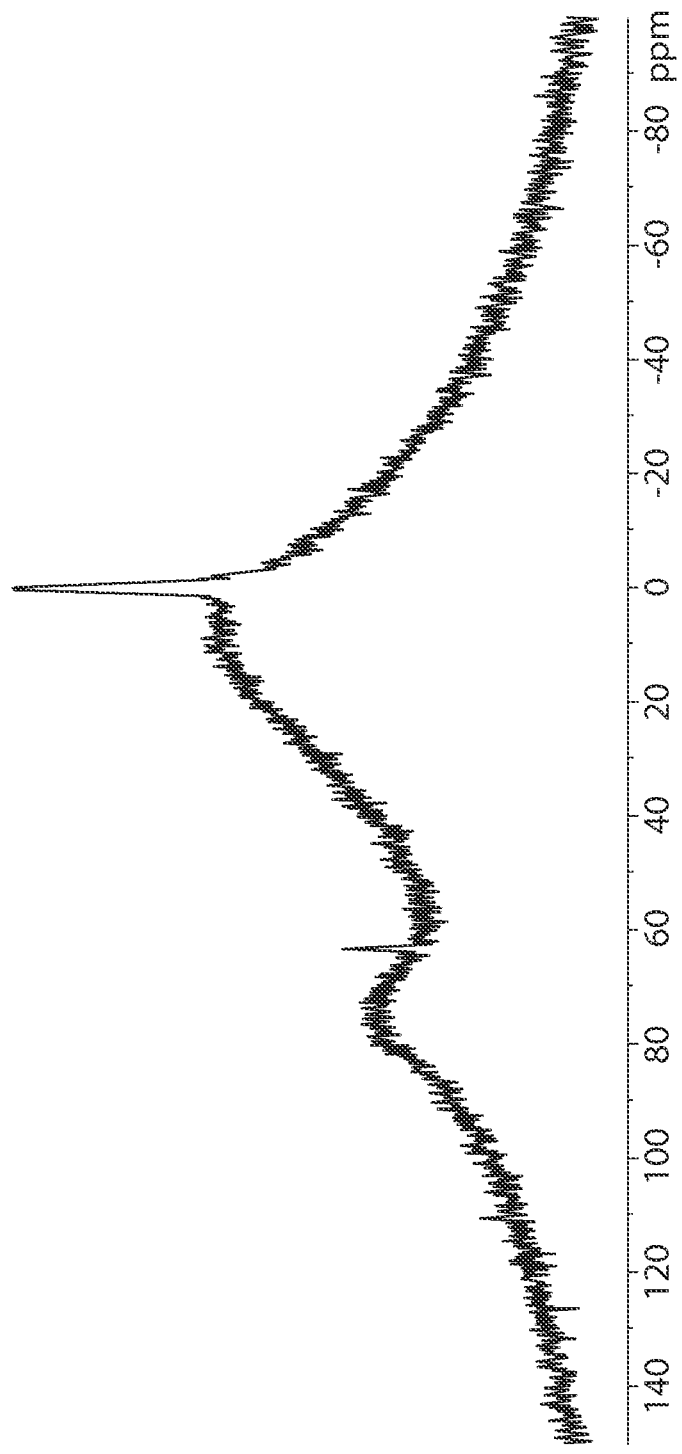
FIG. 2 illustrates an $^{27}$Al NMR spectrogram of the aluminum salt produced according to Example 1.

As illustrated in FIG. 2, the $^{27}Al$ NMR spectrum shows a peak at approximately 70 ppm, representing the $Al_{30}$ polyhydroxyoxoaluminum cation, and a peak at approximately 62.5 ppm, representing the $Al_{13}$ polyhydroxyoxoaluminum cation. The peak ratios show the $Al_{30}$ polyhydroxyoxoaluminum cation as the predominant species detectable by $^{27}Al$ NMR within the aluminum salt. The peak at approximately 0 ppm represents the $Al_m$ monomer, $AlCl_3$. The $^{27}Al$ NMR spectrum has a species distribution including 91.3% Al as $Al_{30}$ polyhydroxyoxoaluminum cation, 5.2% Al as $Al_{13}$ polyhydroxyoxoaluminum cation and 3.5% Al as the $Al_m$ monomer. In other words, using a glycine buffer and a calcium hydroxide inorganic base for a reaction time of 2.5 hours, the aluminum salt included at least 90% Al as $Al_{30}$ polyhydroxyoxoaluminum cation as determined by $^{27}Al$ NMR and was the predominant species detectable by $^{27}Al$ NMR within the aluminum salt.

Example 2

The remainder of the solution from which the aliquot was taken in Example 1 was continuously heated at 95° C. and stirred under reflux for a period of 24 hours. An aliquot was removed and subjected to testing by SEC chromatography and $^{27}Al$ NMR spectroscopy.

Figure 3:
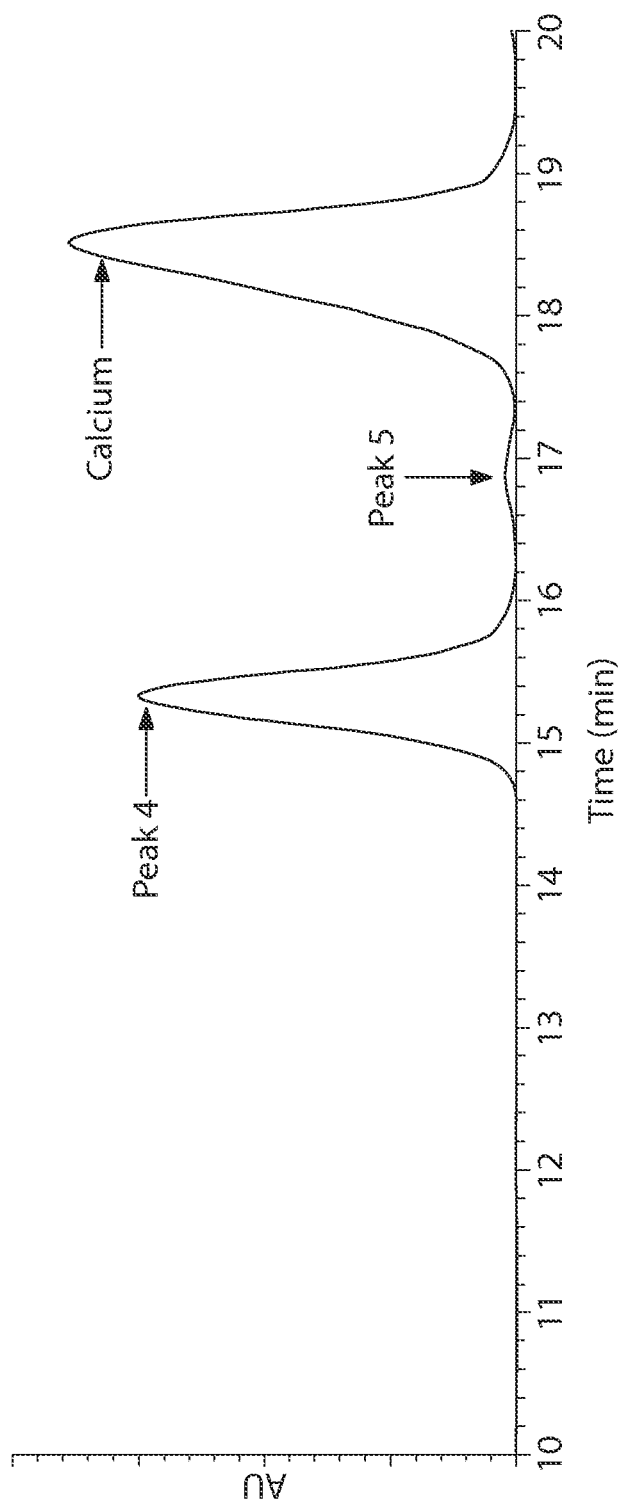
FIG. 3 illustrates an SEC chromatogram of an aluminum salt produced according to Example 2 of the present invention.

As illustrated in FIG. 3, the SEC chromatogram shows, like FIG. 1, exclusively SEC-Peak 4 and SEC-Peak 5. No SEC-Peak 3 species is observed. No SEC-Peak 1 species or SEC-Peak 2 species is observed. The SEC-Peak 4 area comprised 98.2%, i.e. at least 90%, of the total area of Peaks 1, 2, 3, 4 and 5 in the SEC chromatogram. The SEC-Peak 5 area comprised 1.8%, i.e. less than 5%, of the total area of Peaks 1, 2, 3, 4 and 5 in the SEC chromatogram.

Figure 4:
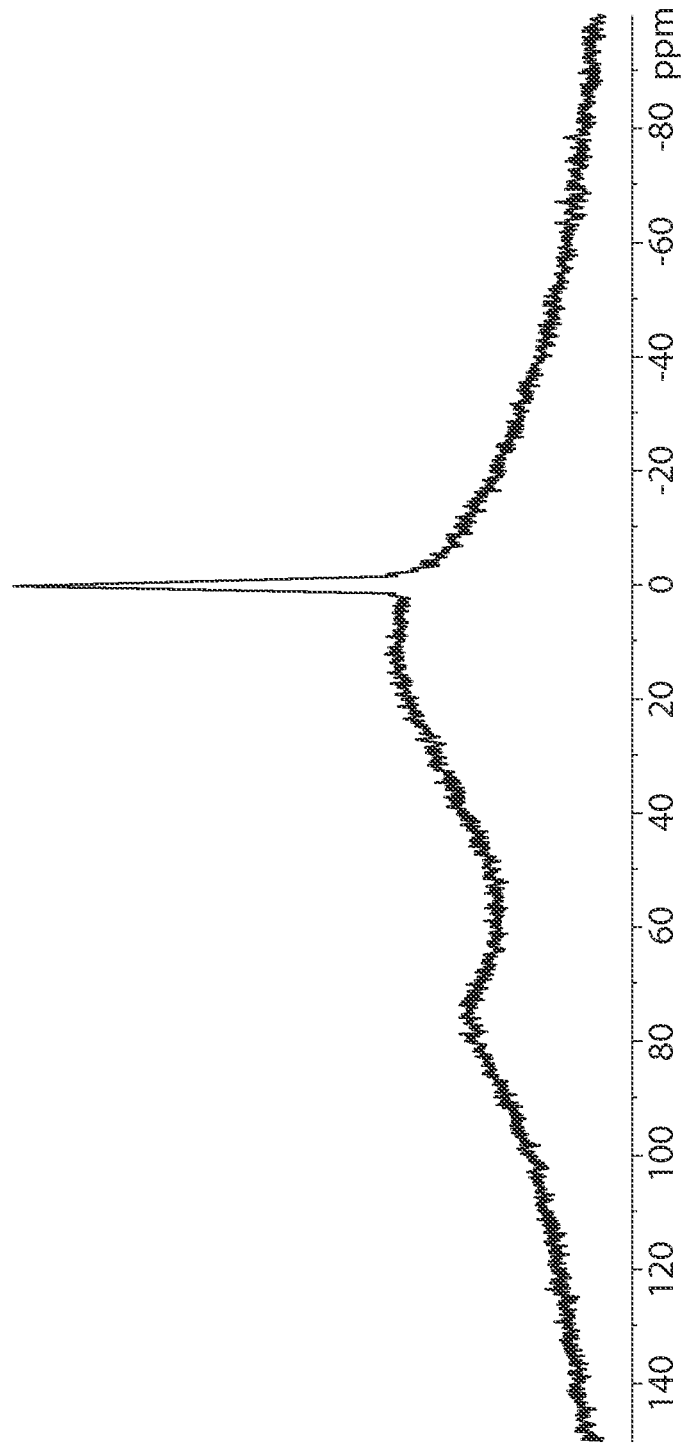
FIG. 4 illustrates an $^{27}$Al NMR spectrogram of the aluminum salt produced according to Example 2.

As illustrated in FIG. 4, the $^{27}$Al NMR spectrum shows a peak at approximately 70 ppm, representing the $Al_{30}$ polyhydroxyoxoaluminum cation, and a peak at approximately 62.5 ppm, representing the $Al_{13}$ polyhydroxyoxoaluminum cation. The peak ratios show, like FIG. 2, the $Al_{30}$ polyhydroxyoxoaluminum cation as the predominant species detectable by $Al^{27}$ NMR within the aluminum salt. The peak at approximately 0 ppm represents the $Al_m$ monomer, $AlCl_3$. However, the peak ratios were changed as compared to Example 1. The $^{27}$Al NMR spectrum has a species distribution including an increased, as compared to Example 1, value of 95.2% Al as $Al_{30}$ polyhydroxyoxoaluminum cation, a decreased value of 0% Al as $Al_{13}$ polyhydroxyoxoaluminum cation (i.e. the $Al_{13}$ polyhydroxyoxoaluminum cation was undetectable) and 4.8% Al as the $Al_m$ monomer.

In other words, prolonged heating of the aluminum salt to react further the aluminum salt, the inorganic acid and the glycine buffer caused complete conversion of the $Al_{13}$ polyhydroxyoxoaluminum cation into the $Al_{30}$ polyhydroxyoxoaluminum cation, and further reduction of the $Al_m$ monomer, $AlCl_3$.

The conversion of the $Al_{13}$ polyhydroxyoxoaluminum cation into the $Al_{30}$ polyhydroxyoxoaluminum cation was achieved without formation of any Peak 3 species detectable by the SEC chromatography. Therefore the antiperspirant efficacy sand stability of the aluminum salt were increased by this reaction not only by increasing the proportion of the $Al_{30}$ polyhydroxyoxoaluminum cation and decreasing the proportion of the $Al_{13}$ polyhydroxyoxoaluminum cation, both of which are Peak 4 species detectable by the SEC chromatography, but also by avoiding any consequential formation of any Peak 3 species detectable by the SEC chromatography which would reduce the antiperspirant efficacy.

Comparative Example 1

Figure 5:
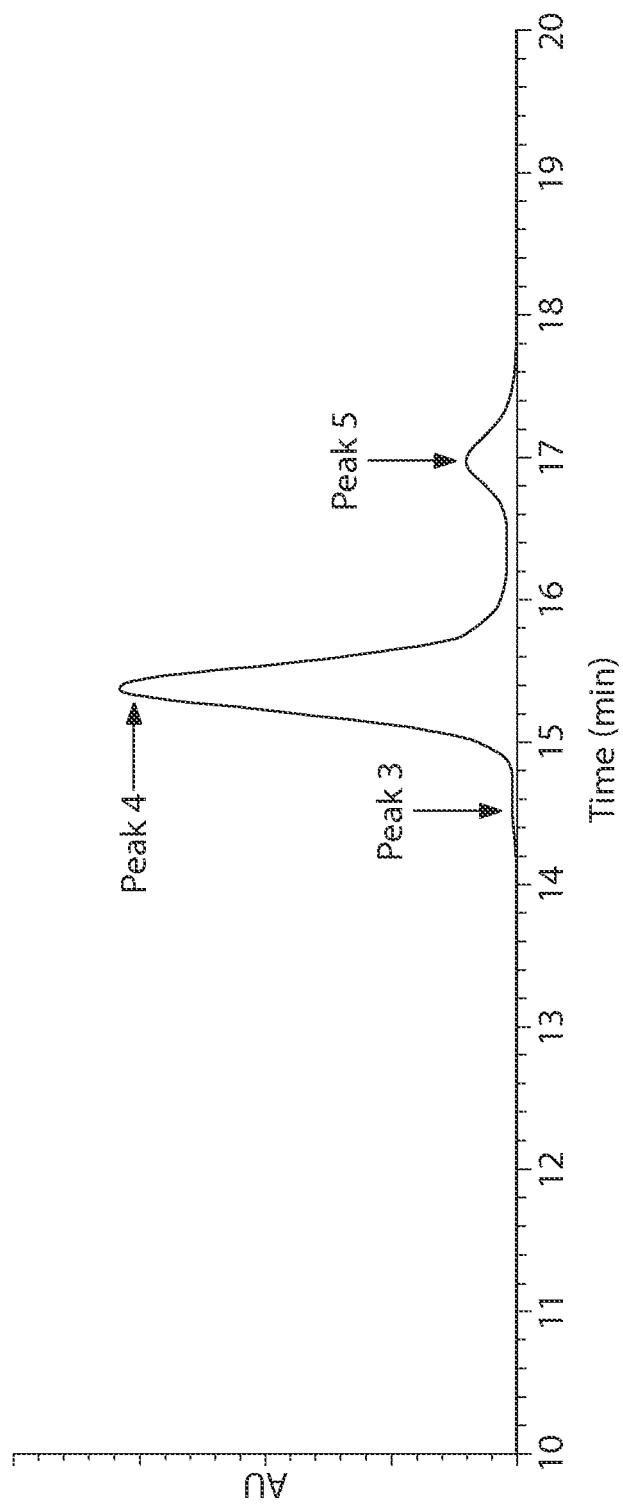
FIG. 5 illustrates an SEC chromatogram of an unpurified aluminum salt produced according to Comparative Example 1 not in accordance with the present invention.

An aqueous solution of 0.18M $AlCl_3.6H_2O$ (180 mmol), without buffer, was heated to 90° C. under vigorous stirring. To this solution, a 2 N NaOH (442.8 mmol) was added dropwise over a 2 hour period until a final molar ratio of OH:Al of 2.46 was achieved. The solution was heated and stirred for an additional 1 hour before being quenched in cold water. The pH after the reaction was 3.9. An aliquot was removed and subjected to testing by SEC chromatography. The result is shown in FIG. 5, the SEC chromatogram showing a dominant SEC-Peak 4, a smaller SEC-Peak 5 and a yet smaller SEC-Peak 3.

Figure 6:
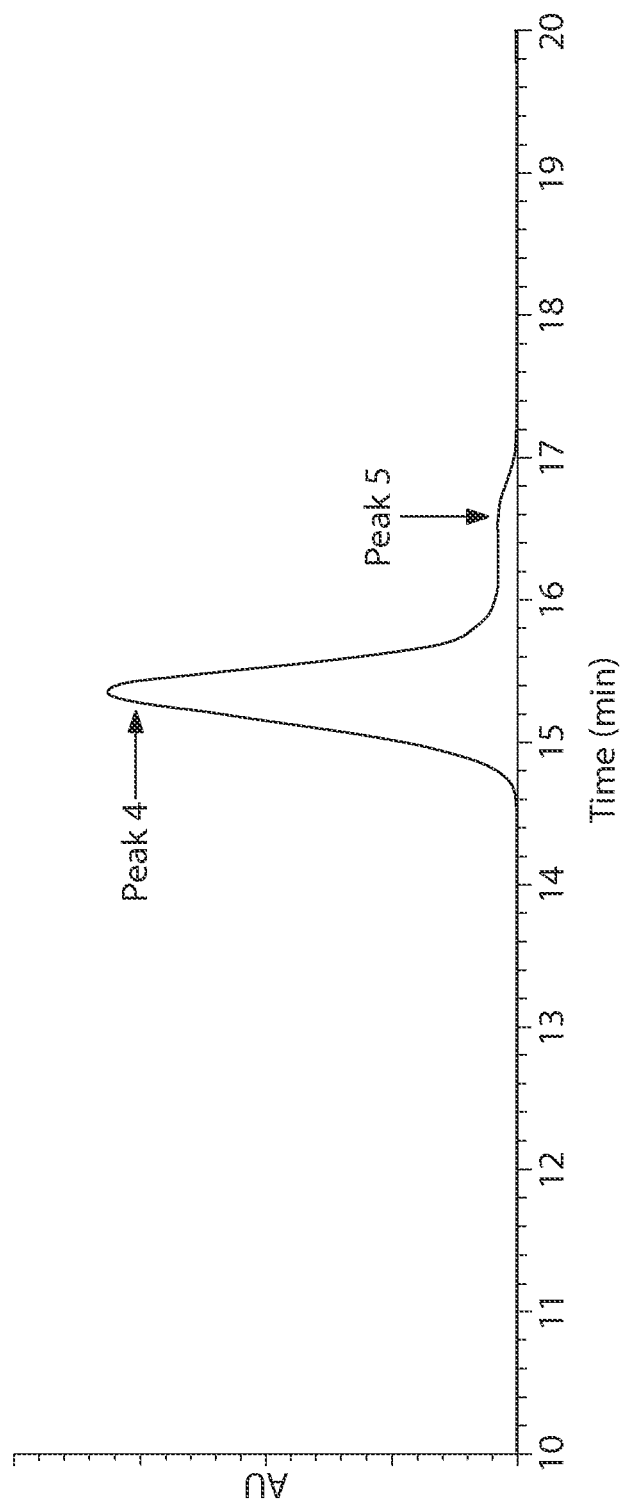
FIG. 6 illustrates an SEC chromatogram of a purified aluminum salt produced according to Comparative Example 1.

The remainder of the reaction solution was subjected to a purification process as follows. An aqueous solution of $NaSO_4$ was added to the reaction flask with a target $Al:SO_4$ molar ratio of 1:1. The resulting precipitate was collected and dissolved in an aqueous solution containing $BaCl_2$ with a target $Ba:SO_4$ molar ratio of 1:1. The filtrate was collected as a purified aluminum salt and subject to testing by SEC chromatography. The result is shown in FIG. 6. The SEC chromatogram shows, as compared to the unpurified aluminum salt, a smaller SEC-Peak 5 and a yet smaller, almost undetectable, SEC-Peak 3, with the dominant SEC-Peak 4 being maintained.

The purified aluminum salt was subjected to testing by $^{27}$Al NMR spectroscopy.

Figure 7:
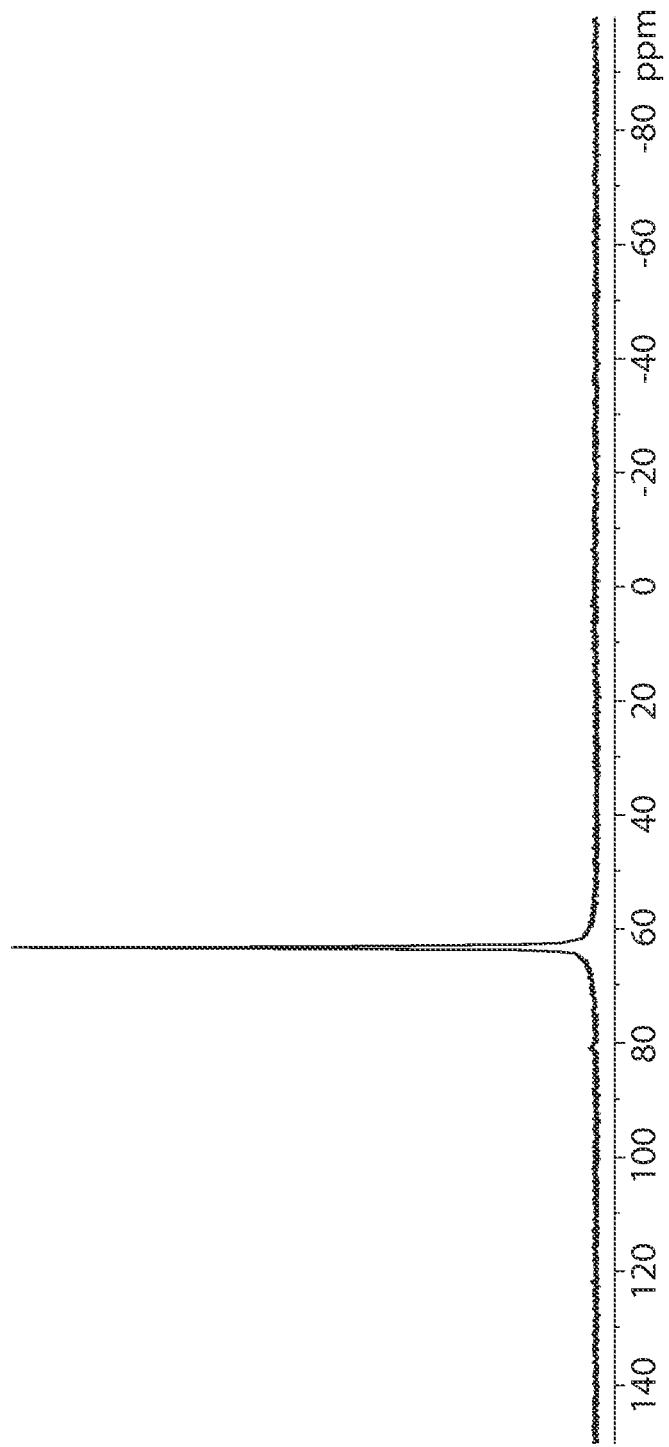
FIG. 7 illustrates an $^{27}$Al NMR spectrogram of the purified aluminum salt produced according to Comparative Example 1.

As illustrated in FIG. 7, the $^{27}$Al NMR spectrum shows a peak at approximately 62.5 ppm, representing the $Al_{13}$ polyhydroxyoxoaluminum cation. There is no peak at approximately 70 ppm, representing the $Al_{30}$ polyhydroxyoxoaluminum cation. The NMR spectrum shows the $Al_{13}$ polyhydroxyoxoaluminum cation as the predominant species detectable by $^{27}$Al NMR within the aluminum salt. There was no peak at approximately 0 ppm which would represent the $Al_m$ monomer. $AlCl_3$. The $^{27}$Al NMR spectrum has a species distribution including 100% Al as $Al_{13}$ polyhydroxyoxoaluminum cation, with 0% Al as $Al_{30}$ polyhydroxyoxoaluminum cation, and 0% Al as the $Al_m$ monomer.

Comparative Example 2

An aqueous solution of 0.5M $AlCl_3.6H_2O$ (200 mmol), without buffer, was heated to 95° C. under vigorous stirring. To this solution, a 2 N NaOH (480 mmol) was added dropwise over a 2 hour 30 minute period until a final molar ratio of OH:Al of 2.40 was achieved. The solution was heated and stirred for an additional 48 hours before being quenched in cold water. The pH after the reaction was 3.6.

Figure 8:
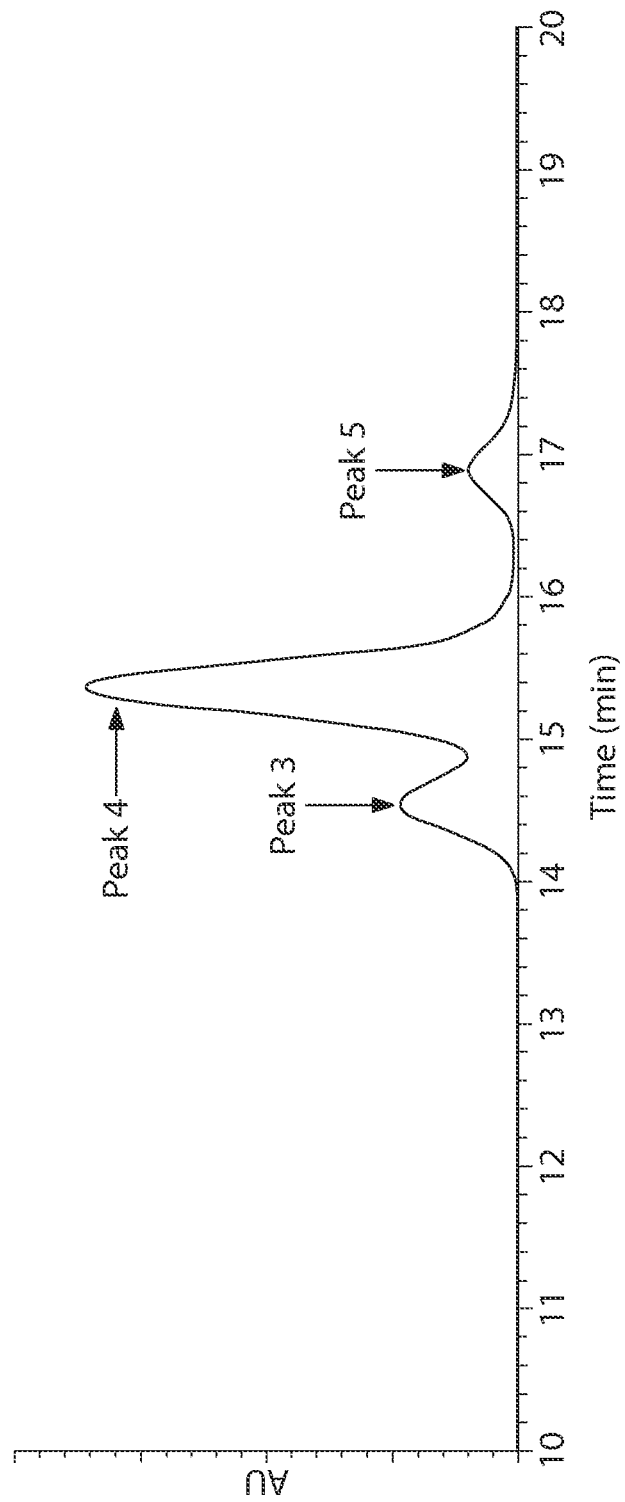
FIG. 8 illustrates an SEC chromatogram of an unpurified aluminum salt produced according to Comparative Example 2 not in accordance with the present invention.

An aliquot was removed and subjected to testing by SEC chromatography. The result is shown in FIG. 8, the SEC chromatogram showing a dominant SEC-Peak 4, a smaller but significant SEC-Peak 3 and a yet smaller SEC-Peak 5.

Figure 9:
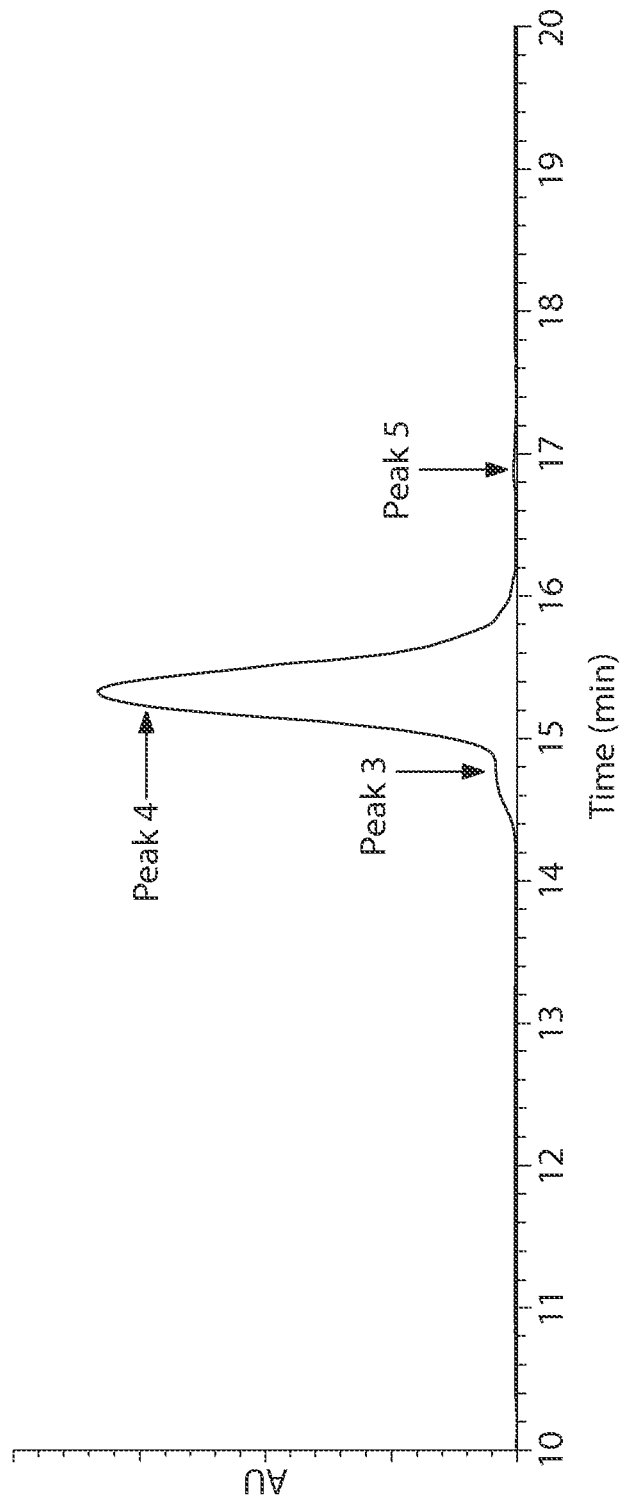
FIG. 9 illustrates an SEC chromatogram of a purified aluminum salt produced according to Comparative Example 2.

The reaction solution was freeze-dried and the resulting powder was subjected to a purification process by fractionation using a 1.1 cm diameter by 15 cm long column packed with polyacrylamide gel (Bio-Gel P4, available in commerce from Bio-Rad). The resulting purified aluminum salt was subjected to testing by SEC chromatography. The result is shown in FIG. 9. The SEC chromatogram shows, as compared to the unpurified aluminum salt of FIG. 8, a smaller SEC-Peak 3 and a smaller SEC-Peak 5, with the dominant SEC-Peak 4 being maintained.

The purified aluminum salt was subjected to testing by $^{27}$Al NMR spectroscopy.

Figure 10:
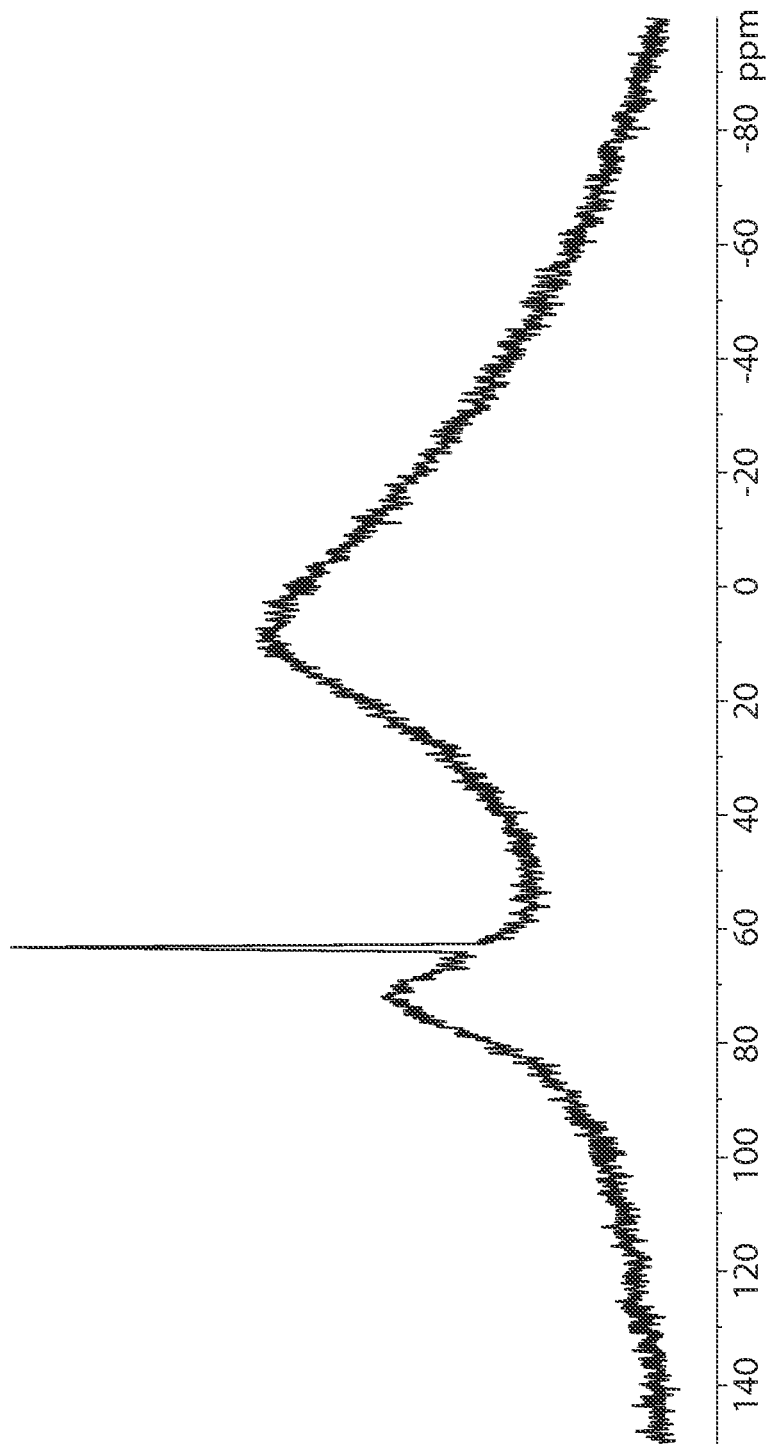
FIG. 10 illustrates an $^{27}$Al NMR spectrogram of the purified aluminum salt produced according to Comparative Example 2.

As illustrated in FIG. 10, the $^{27}$Al NMR spectrum shows a smaller peak at approximately 62.5 ppm, representing the $Al_{13}$ polyhydroxyoxoaluminum cation and a larger peak at approximately 70 ppm, representing the $Al_{30}$ polyhydroxyoxoaluminum cation. The NMR spectrum shows the $Al_{30}$ polyhydroxyoxoaluminum cation as the predominant species detectable by $^{27}$Al NMR within the aluminum salt, but significant $Al_{13}$ polyhydroxyoxoaluminum cation too. There was no peak at approximately 0 ppm which would represent the $Al_m$ monomer, $AlCl_3$. The 27Al NMR spectrum has a species distribution including 11.5% Al as $Al_{13}$ polyhydroxyoxoaluminum cation, 88.5% Al as $Al_{30}$ polyhydroxyoxoaluminum cation, and 0% Al as the $Al_m$ monomer.

The Examples and Comparative Examples collectively show that the use of the buffer, such as glycine, combined with a prolonged reaction time at elevated temperature, typically more than 6 hours or more than 12 hours, can cause conversion of a substantial proportion of, even all of, the $Al_{13}$ polyhydroxyoxoaluminum cation into the $Al_{30}$ polyhydroxyoxoaluminum cation, without causing the creation of any SEC-Peak 3 aluminum-containing molecules which would reduce antiperspirant efficacy. The SEC chromatogram of the resultant aluminum salt can exhibit a Peak 4 area of at least 90% of a total area of Peaks 1, 2, 3, 4 and 5 in the SEC chromatogram, and with zero detectable Peak 3 and Peak 5 species, as well as zero detectable Peak 1 and Peak 2 species. As Example 1 shows, even the use of the buffer without a prolonged reaction time at elevated temperature can provide an aluminum salt in an antiperspirant active composition which has a high proportion, greater than 90% $Al_{30}$ polyhydroxyoxoaluminum cation in the Al species detectable by NMR, and a high SEC Peak-4 area and a low, less than 10%, even less than 6%, SEC-Peak 3 area.

The conversion of the $Al_{13}$ polyhydroxyoxoaluminum cation into the $Al_{30}$ polyhydroxyoxoaluminum cation does not, per se, increase the Peak 4 area because both the $Al_{13}$ polyhydroxyoxoaluminum cation and the $Al_{30}$ polyhydroxyoxoaluminum cation elute under Peak 4 when the aluminum salt is subjected to SEC chromatography. However, since the $Al_{30}$ polyhydroxyoxoaluminum cation has a higher stability than the $Al_{13}$ polyhydroxyoxoaluminum cation, the resultant aluminum salt has a higher stability in an antiperspirant active composition.

Therefore the provision of an antiperspirant active composition which has a high proportion, at least 90% $Al_{30}$ polyhydroxyoxoaluminum cation in the Al species detectable by NMR, and a high, at least 90% SEC Peak-4 area and a low, less than 10%, even less than 6%, even less than 5%, or even undetectable, i.e. 0% SEC-Peak 3 area, provides the combination of high antiperspirant efficacy and high stability of the antiperspirant active composition.

It will be readily apparent to those skilled in the art that various selections of compositional and/or process parameters, such as the inorganic base, buffer and heating time and/or temperature, may be made individually or in combination based on the present disclosure and the knowledge of the skilled person to provide modifications to the Example which can still achieve an aluminum salt for use as an antiperspirant active composition having the stability and antiperspirant efficacy provided by the Examples and within the scope of the appended claims.

What is claimed is:

1. A method of making an antiperspirant active composition comprising:
    I) heating an aqueous solution containing a first aluminum salt having an aluminum to chloride molar ratio of 0.3:1 to 3:1 and a buffer, wherein the buffer is an amino acid or betaine and a molar ratio of buffer to aluminum is at least 0.1:1, at a temperature of 50° C. to 100° C. for a period of time of 1 hour to 6 hours to obtain a first aluminum salt solution;
    II) adding to the first aluminum salt solution an aqueous solution of an inorganic base to obtain a second pH adjusted aluminum salt solution having an OH:Al molar ratio of at most 2.6:1 and a pH of 2 to 5;
    III) heating the second pH adjusted aluminum salt solution at a temperature of 50° C. to 100° C. for a period of time of at least 6 hours to obtain a third aluminum salt solution containing a third aluminum salt exhibiting an $^{27}$Al NMR spectrum with a species distribution including at least 95% $Al_{30}$ polyhydroxyoxoaluminum cation as the predominant species detectable by $^{27}$Al NMR within the third aluminum salt; and
    IV) optionally adding an aqueous solution containing a zirconium compound to the second pH adjusted aluminum salt solution to thereby obtain a second pH adjusted aluminum-zirconium salt solution having a molar ratio of aluminum to zirconium of 5:1 to 10:1.

2. The method of claim 1, wherein the aluminum salt exhibits a SEC chromatogram having a SEC Peak 4 area of at least 90% of a total area of Peaks 1, 2, 3, 4, and 5 in the SEC chromatogram.

3. The method of claim 1, wherein the buffer is glycine.

4. The method of claim 1, wherein the inorganic base includes at least one member chosen from calcium hydroxide, strontium hydroxide, barium hydroxide, calcium oxide, strontium oxide, barium oxide, calcium carbonate, barium carbonate, strontium carbonate, yttrium hydroxide, yttrium oxide, and yttrium carbonate.

5. The method of claim 4, wherein the inorganic base is calcium hydroxide.

6. The method of claim 1, wherein the second pH adjusted aluminum salt solution has an OH to Al molar ratio of 2:1 to 2.5:1.

7. The method claim 1, wherein the first aluminum salt is an aluminum chloride compound chosen from aluminum trichloride, aluminum chlorohexahydrate, and aluminum dichlorohydrate.

8. The method of claim 1, wherein the composition further comprises zirconium and step IV) is present in the method.

9. The method of claim 8, wherein the zirconium compound is $ZrOCl_2$ $8H_2O$.

10. The method of claim 1, wherein the $^{27}$Al NMR spectrum has a species distribution including at most 5% $Al_{13}$ polyhydroxyoxoaluminum cation in the species detectable by $^{27}$Al NMR within the third aluminum salt.

11. The method of claim 10, wherein the $^{27}$Al NMR spectrum has a species distribution including no $Al_{13}$ polyhydroxyoxoaluminum cation in the species detectable by $^{27}$Al NMR within the third aluminum salt.

12. The method of claim 1, wherein the $^{27}$Al NMR spectrum has a species distribution including at most 5% $Al_m$, $Al_m$ comprising an aluminum- and chloride-containing monomer, in the species detectable by $^{27}$Al NMR within the third aluminum salt.

13. The method of claim 1, wherein the third aluminum salt has a SEC Peak 4 area of at least 95% of a total area of Peaks 1, 2, 3, 4, and 5 in the SEC chromatogram.

14. The method of claim 1, wherein the third aluminum salt has a SEC Peak 3 area of less than 5% of a total area of Peaks 1, 2, 3, 4, and 5 in the SEC chromatogram.

15. The method of claim 14, wherein the third aluminum salt has no SEC Peak 3 area in the SEC chromatogram.

16. The method of claim 1, wherein the third aluminum salt has a SEC Peak 5 area of less than 5% of a total area of Peaks 1, 2, 3, 4, and 5 in the SEC chromatogram.

17. The method according to claim 1, wherein in step III) the period of time is at least 12 hours.

* * * * *